US006987833B2

(12) United States Patent
Du et al.

(10) Patent No.: US 6,987,833 B2
(45) Date of Patent: Jan. 17, 2006

(54) METHODS AND APPARATUS FOR IDENTIFICATION AND IMAGING OF SPECIFIC MATERIALS

(75) Inventors: Yanfeng Du, Clifton Park, NY (US); John Eric Tkaczyk, Delanson, NY (US)

(73) Assignee: General Electric Company, Niskayuna, NY (US)

( * ) Notice: Subject to any disclaimer, the term of this patent is extended or adjusted under 35 U.S.C. 154(b) by 80 days.

(21) Appl. No.: 10/687,131

(22) Filed: Oct. 16, 2003

(65) Prior Publication Data

US 2005/0084069 A1 Apr. 21, 2005

(51) Int. Cl.
*G01N 23/087* (2006.01)
(52) U.S. Cl. .............................. 378/98.9; 378/5; 378/53
(58) Field of Classification Search ................... 378/5, 378/16, 18, 53, 57, 98.9, 98.11, 207; 600/407, 600/425, 431
See application file for complete search history.

(56) References Cited

U.S. PATENT DOCUMENTS

| 4,029,963 A | * | 6/1977 | Alvarez et al. ................ 378/5 |
| 4,686,695 A | * | 8/1987 | Macovski ....................... 378/5 |
| 5,123,037 A | * | 6/1992 | Picard et al. ............... 378/98.2 |
| 5,247,559 A | * | 9/1993 | Ohtsuchi et al. .............. 378/53 |
| 5,253,282 A | * | 10/1993 | Pelc ........................... 378/98.2 |
| 5,485,492 A | * | 1/1996 | Pelc ............................... 378/5 |
| 6,076,400 A | | 6/2000 | Bechwati et al. |
| 6,078,642 A | | 6/2000 | Simanovsky |
| 6,574,302 B2 | * | 6/2003 | Adriaansz .................... 378/54 |
| 6,597,759 B2 | * | 7/2003 | Mazess et al. ................ 378/53 |
| 6,614,874 B2 | | 9/2003 | Avinash |
| 6,735,273 B2 | * | 5/2004 | Flohr et al. ..................... 378/5 |
| 6,813,333 B2 | * | 11/2004 | Karau et al. .................... 378/4 |
| 6,836,528 B2 | * | 12/2004 | Reddy et al. ................... 378/5 |
| 6,898,263 B2 | * | 5/2005 | Avinash et al. ................ 378/4 |
| 2003/0152258 A1 | | 8/2003 | Jabri et al. |
| 2004/0101088 A1 | * | 5/2004 | Sabol et al. .................... 378/4 |
| 2004/0136491 A1 | * | 7/2004 | Iatrou et al. .................... 378/4 |
| 2004/0184574 A1 | * | 9/2004 | Wu et al. ........................ 378/5 |

* cited by examiner

*Primary Examiner*—Allen C. Ho
(74) *Attorney, Agent, or Firm*—Fletcher Yoder

(57) ABSTRACT

A method for analyzing materials in an object includes acquiring x-ray projection data of the object at high energy and at low energy for a plurality of views. The acquired x-ray projection data is utilized in a material decomposition to determine material densities at each pixel for two selected basis materials. A composition of an object at each pixel is determined utilizing a determined mapping of material density regions for the two selected basis materials. An image indicative of the composition of the object is displayed utilizing the determined composition.

19 Claims, 8 Drawing Sheets

METHODS AND APPARATUS FOR IDENTIFICATION AND IMAGING OF SPECIFIC MATERIALS

BACKGROUND OF THE INVENTION

This invention relates generally to methods and apparatus useful for determining the composition of materials under study, and more particularly to methods and apparatus for analyzing and/or imaging specific materials in objects under study.

Because many known CT detection systems do not provide energy resolution, it is not possible to provide material characterization information for an object under study. For example, a highly attenuating material with low density can produce the same CT number in an image as a less attenuating material with high density. As a result, known computed tomographic (CT) images do not differentiate materials that have similar density but different atomic numbers, and images may look substantially uniform even though an object under study has variations in its material composition. In addition, beam-hardening artifacts, such as non-uniformity, shading, and streaking can result from the non-linear relationship between x-ray attenuation and path lengths for polychromatic x-ray beams in CT imaging systems. Also, known CT imaging systems do not provide quantitative image values. Instead, the same material at different locations can show different CT numbers.

At least one known dual energy decomposition algorithm is known that represents material-specific characteristics as a two-parameter basis set. Thus, by encoding each of these parameters individually, two separate images can be formed using a CT system. In at least one known system, a single slice image is acquired using a single slice CT detector system, using two different x-ray beam filters or two different x-ray tube voltages (kVp's). The different filters or voltages are used to obtain scan the same slice of an object. The two scans are not performed simultaneously, but instead are performed at slightly different times, e.g., sequentially. In another known system, energy sensitive scanning is performed by using an energy sensitive detector system such as a photon counting detector. In either case, the two energy dependent data sets are used with an appropriate material decomposition algorithm to produce two images, each representing one of the two basis materials.

In two basis material decomposition images produced by known imaging systems, the imaging value for each pixel in an image is equal to the material density for the corresponding basis material. Any material other than the two basis materials will show up in both images, with the image pixel value being proportional to the density of the non-basis material.

Using known two basis material decomposition algorithms, any material other than the two basis materials appears in both basis material images with an incorrect density. This contamination reduces the visibility of the basis materials in the images, and also results in density errors in quantification applications.

BRIEF DESCRIPTION OF THE INVENTION

Some configurations of the present invention therefore provide a method for analyzing materials in an object. The method includes acquiring x-ray projection data of the object at high energy and at low energy for a plurality of views. The acquired x-ray projection data is utilized in a material decomposition to determine material densities at each pixel for two selected basis materials. A composition of an object at each pixel is determined utilizing a determined mapping of material density regions for the two selected basis materials. An image indicative of the composition of the object is displayed utilizing the determined composition.

Another aspect of the present invention provides a method for analyzing materials in an object that includes acquiring x-ray projection data of the object at high energy and at low energy for a plurality of views. The acquired x-ray projection data is utilized in a material decomposition to determine material densities at each pixel for two selected basis materials. A determined mapping of material density regions for the two selected basis materials is utilized to filter pixels of an image of the object corresponding to one or more compositions of interest, and an image indicative of the locations of composition of interest of the object is displayed.

Still other aspects of the present invention provide an apparatus for analyzing materials in an object. The apparatus includes an x-ray source and a detector configured to acquire projection data at high and low energies for a plurality of views. The apparatus also includes a computer, a storage device, and a display. The apparatus is configured to acquire x-ray projection data of the object at high energy and at low energy for a plurality of views utilizing the x-ray source and the detector. The apparatus is further configured to process the acquired x-ray projection data utilizing the computer and the storage device to determine material densities at each pixel for two selected basis materials and to determine a composition of an object at each pixel utilizing the computer and a determined mapping of material density regions for the two selected basis materials in the storage device. The display is configured to display an image indicative of the composition of the object utilizing the determined composition.

In yet another aspect of the present invention, there is provided an apparatus for analyzing materials in an object. The apparatus includes an x-ray source and a detector configured to acquire projection data at high and low energies for a plurality of views, a computer, a storage device, and a display. The apparatus is configured to acquire x-ray projection data of the object at high energy and at low energy for a plurality of views utilizing the x-ray source the said detector. The apparatus is also configured to process the acquired x-ray projection data utilizing the computer and the storage device to determine material densities at each pixel for two selected basis materials and to utilize the computer and a determined mapping of material density regions for the two selected basis materials in the storage device to filter pixels of an image of the object corresponding to one or more compositions of interest. The display is used to display an image indicative of the locations of composition of interest of the object.

It will thus be appreciated that configurations of the present invention are capable of providing quantitative material information. Some configurations of the present invention further provide improved target material visibility and quantification accuracy and/or provide decomposition into more than one material.

DETAILED DESCRIPTION OF THE INVENTION

Figure 1:
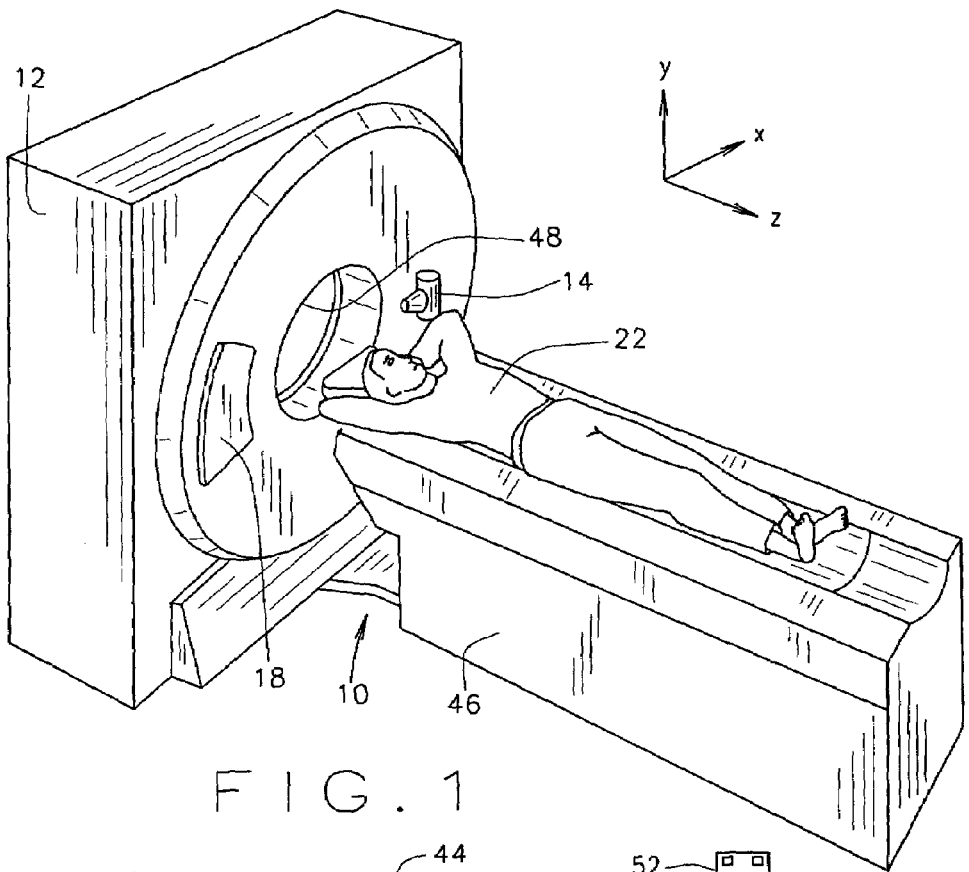
FIG. 1 is a pictorial view of a CT imaging system embodiment.

Example embodiments of methods and apparatus for multiple material decomposition for energy discrimination are described below in more detail. A technical effect of the methods and apparatus described herein include at least one of facilitating the extraction of information concerning a object utilizing a CT imaging system, generation of images representative of a plurality of different materials contained within such an object, and automated identification of materials contained within an object.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 2:
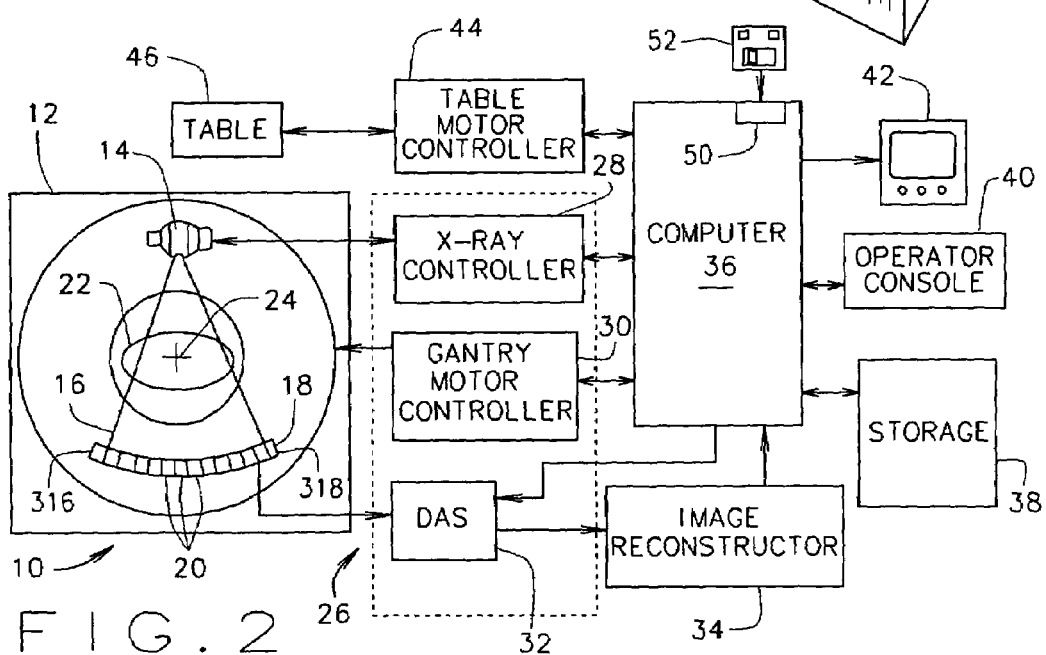
FIG. 2 is a block schematic diagram of the system illustrated in FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has an x-ray tube 14 (also called x-ray source 14 herein) that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22 between array 18 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to fourth generation CT systems (stationary detector—rotating x-ray source) and fifth generation CT systems (stationary detector and x-ray source). Additionally, it is contemplated that the benefits of the invention accrue to imaging modalities other than CT. Additionally, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

To provide material decomposition, some configurations of CT detector array include two different x-ray beam filters (not shown), or x-ray tube 14 is operated at two different x-ray tube voltages (kVp's). The different filters or voltages are used to obtain scans of the same slice or slices of object 22. The two scans are not performed simultaneously in these configurations. Sequential scans of the same slice or slices are satisfactory in studies in which little movement is expected in object 22 between scans. Some other configurations provide an energy sensitive detector array 18, such as a photon counting detector, for energy sensitive scanning. These configurations allow the simultaneous acquisition of scans at different energies. In either case, the two energy dependent data sets are used with an appropriate material decomposition algorithm to produce two images, each representing one of the two basis materials.

In some configurations of the present invention, a CT imaging system 10 acquires dual energy projection measurement data and processes the data to provide two or more images. Each of these images represents a different material signature of object 22 under study. Energy discrimination CT is used in which a CT imaging system is used to separately detect two regions of photon energy spectrum, namely, a low-energy portion and a high-energy portion of an incident x-ray spectrum.

More particularly, in various configurations of the present invention, the measured x-ray attenuation for a material at two or more x-ray energies is decomposed into a linear combination of the attenuation for two basis materials:

$$\mu_m = c_m \mu_A(E) + d_m \mu_B(E), \tag{1}$$

where:

$\mu_m$ (E) is a measured attenuation coefficient for material m (an arbitrary material) at energy E;

$c_m$ is a linear coefficient for a first material A;

$d_m$ is a linear coefficient for a second material B;

$\mu_A$ (E) is an attenuation coefficient for material A at energy E; and $\mu_B$ (E) is an attenuation coefficient for material B at energy E.

Figure 3:
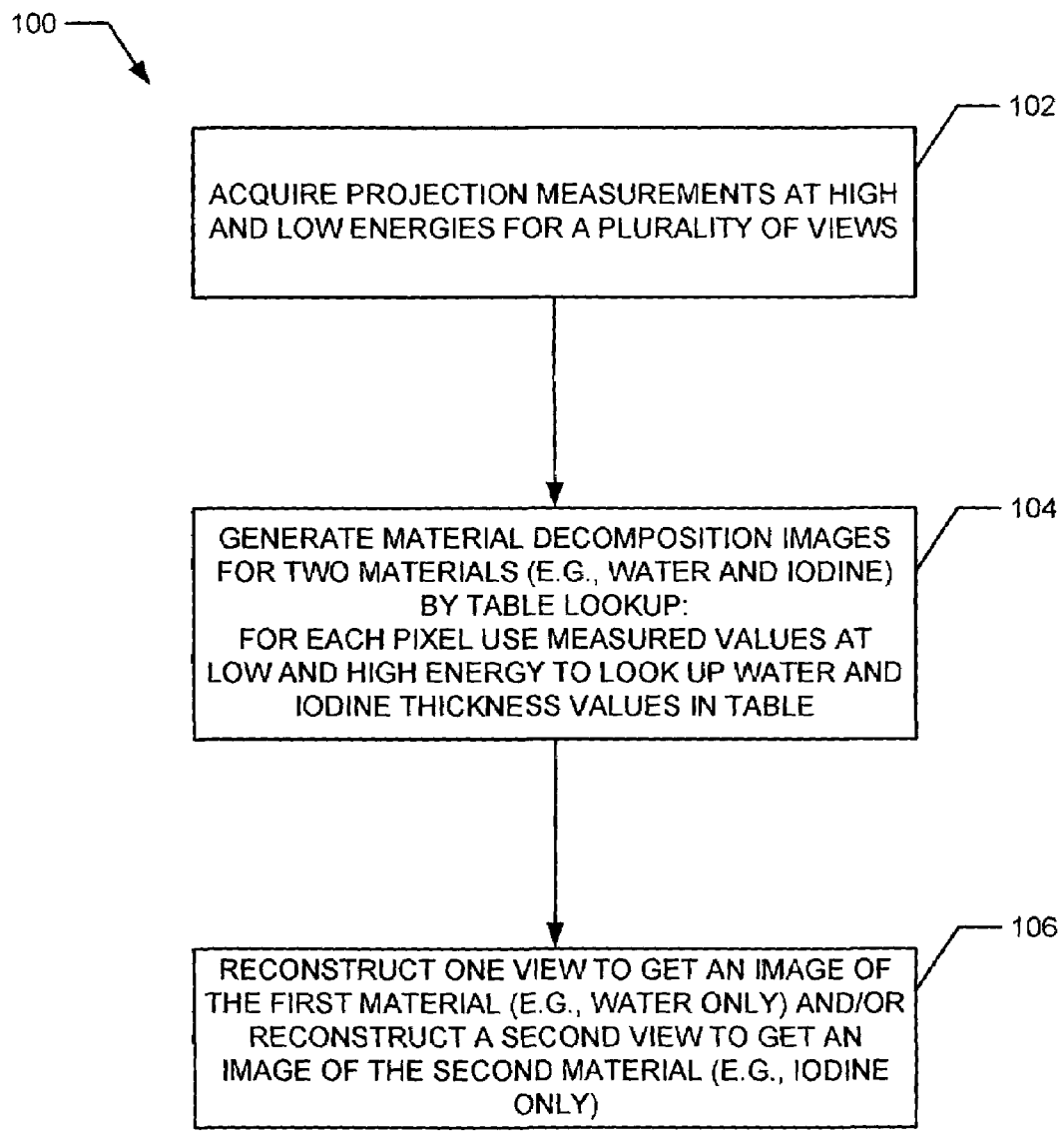
FIG. 3 is a flow chart of a configuration of the present invention used to prepare images from projection measurements at high and low energies for a plurality of views of an object.

Thus, in some configurations of the present invention and referring to flow chart 100 of FIG. 3, a technical effect of imaging system 10 is achieved by a user by operating imaging system 10 to obtain projection measurements at high and low energies for multiple views at 102. Computer 36 and/or storage device 38 are used in some configurations to generate material decomposition images at 104 for two selected materials using any suitable method, such as one using table look-ups. In such configurations, a two-dimensional table is stored in memory 38 and/or in computer 36. This two-dimensional table is referenced using two indices, one of which corresponds to pixel values of the low energy image and the other of which corresponds to values of corresponding pixels of the high energy image. The content of the memory at this location is a list of two values of ρ, namely, $\rho_{mA}$ and $\rho_{mB}$, corresponding to densities of materials A and B. The values $\rho_{mA}$ and $\rho_{mB}$ are inferred as densities of A and B, respectively, at the pixel location. (The arrangement of the table in memory is left as a design choice. For example, some configurations provide two separate tables in memory, one providing $\rho_{mA}$ and the other providing $\rho_{mB}$, rather than a single table in memory that provides both entries.)

In some medical imaging applications, water and iodine can usefully be selected as material A and material B, respectively, but neither the invention itself nor its medical imaging applications are limited to this selection of materials. Using the values $\rho_{mA}$ and $\rho_{mB}$ obtained in the table, images of only the inferred densities of each material are reconstructed in some configurations at 106.

Figure 4:
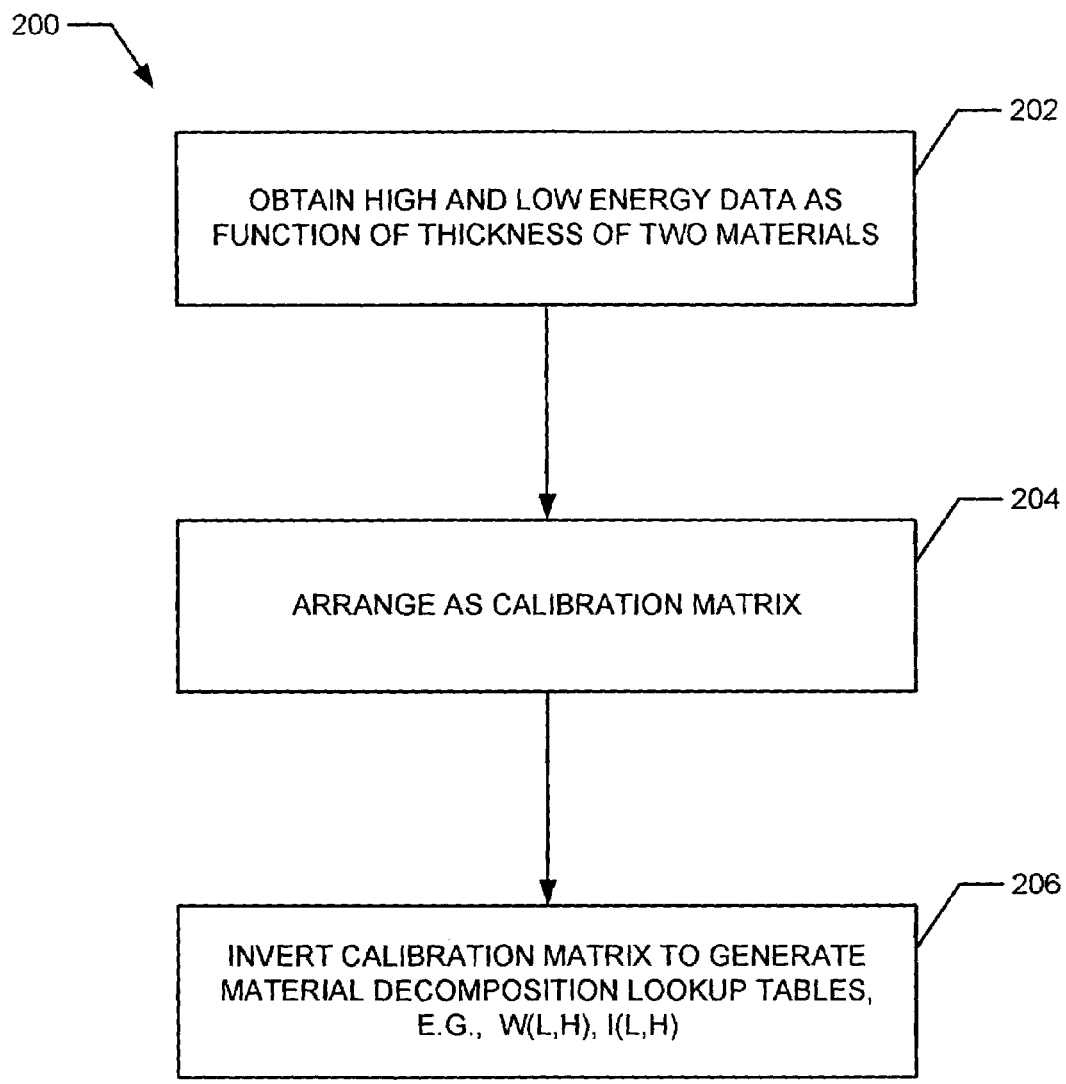
FIG. 4 is a flow chart of a method useful for obtaining a calibration matrix used in the configuration of the present invention represented by the flow chart of FIG. 3.

In some configurations and referring to flowchart 200 of FIG. 4, the contents of the table in memory referred to above is predetermined by a user, a supplier, or another entity by operating an imaging system 10 or other x-ray system. The system is operated to achieve a technical effect of obtaining high and low energy data as a function of thickness of material A and of material B at 202. This information is used to generate a calibration matrix at 204, and inverted at 206 to generate the material decomposition lookup table. Although a plurality of measurements are required at 202 to obtain the needed data, the calibration procedure represented by flowchart 200 need only be performed once for materials A and B. It will be noted that configurations of the present invention may be provided with preprogrammed tables, or tables that may be programmed from machine readable media, such as media 52. In some configurations, the tables may be determined by a user of imaging system 10 at a time chosen by the user, upon the user's recognition of the need for a particular table in a particular situation.

Figure 5:
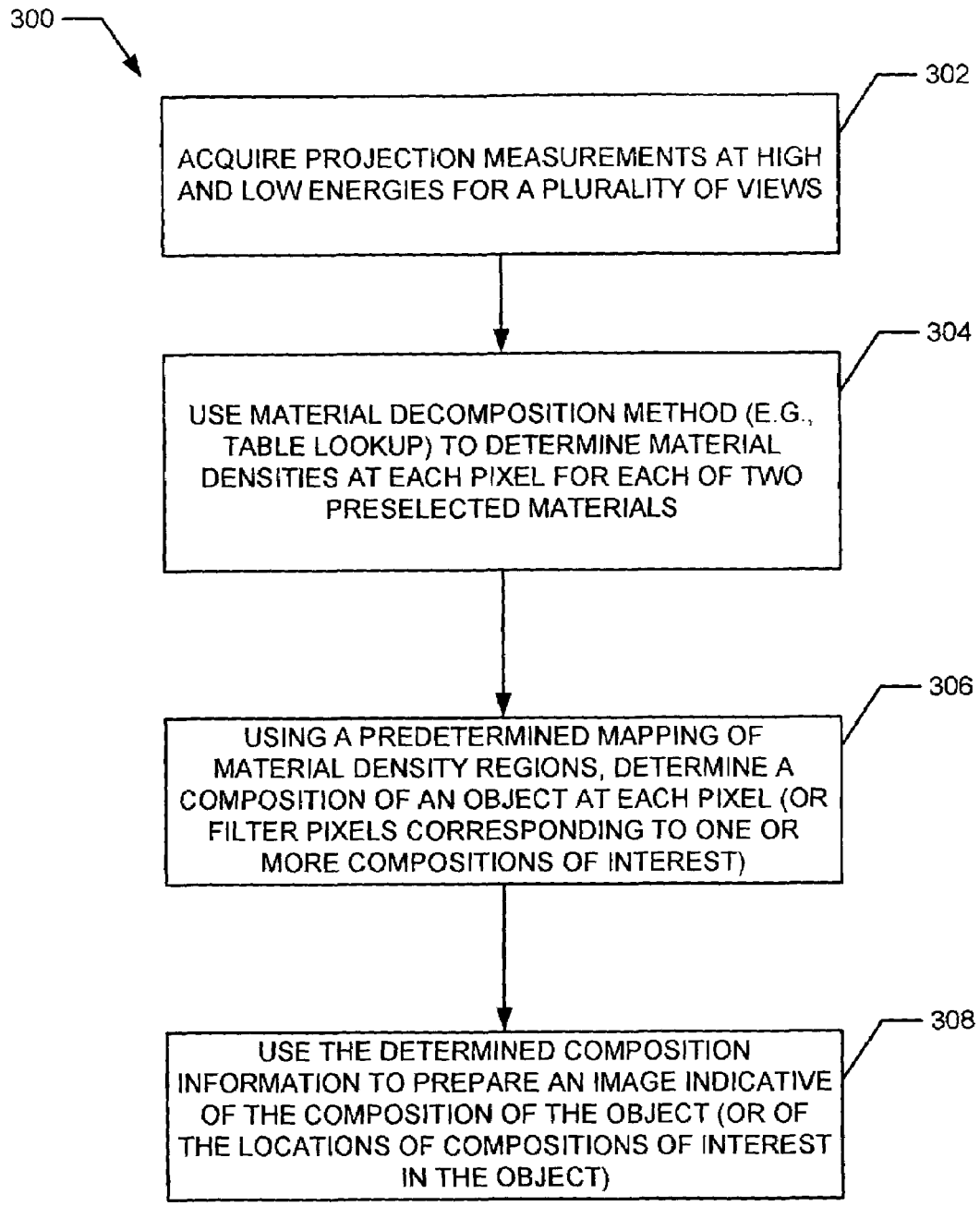
FIG. 5 is a flow chart representative of configurations of the present invention that produce an image indicative of the composition of an object or an image showing locations of one or more composition of interest within the object.

In various configurations of the present invention and referring to flowchart 300 of FIG. 5, the technical effect of imaging system 10 is achieved by a user operating imaging system 10 to acquire projection measurements for a plurality of views of an object 22 at high and low energies at 302. At 304, irrespective of the actual composition of object 22, a material decomposition is performed at using the table derived for materials A and B. The two linear coefficients derived from this linear combination are distinctive for the various materials and will characterize the effective atomic number of a material. Using the two linear coefficients thus derived enables configurations 10 of the present invention to reconstruct a material density for any target 22 material and to encode an image. This reconstruction creates separate cross-sectional or volumetric data sets for each target 22 material. As a result, visibility and quantification accuracy of composite and spatially variable objects is improved.

More particularly, in CT system 10, a CT number in a reconstructed image represents a linear attenuation coefficient:

$$\alpha = \rho \cdot \mu_m$$

where $\rho$ is a material density of object 22 having units g/cm$^3$, $\mu_m$ is a mass attenuation coefficient having units cm$^2$/g, and a is a linear attenuation coefficient having units cm$^{-1}$. Thus, if the material of object 22 is known, one can determine the density $\rho$.

Figure 6:
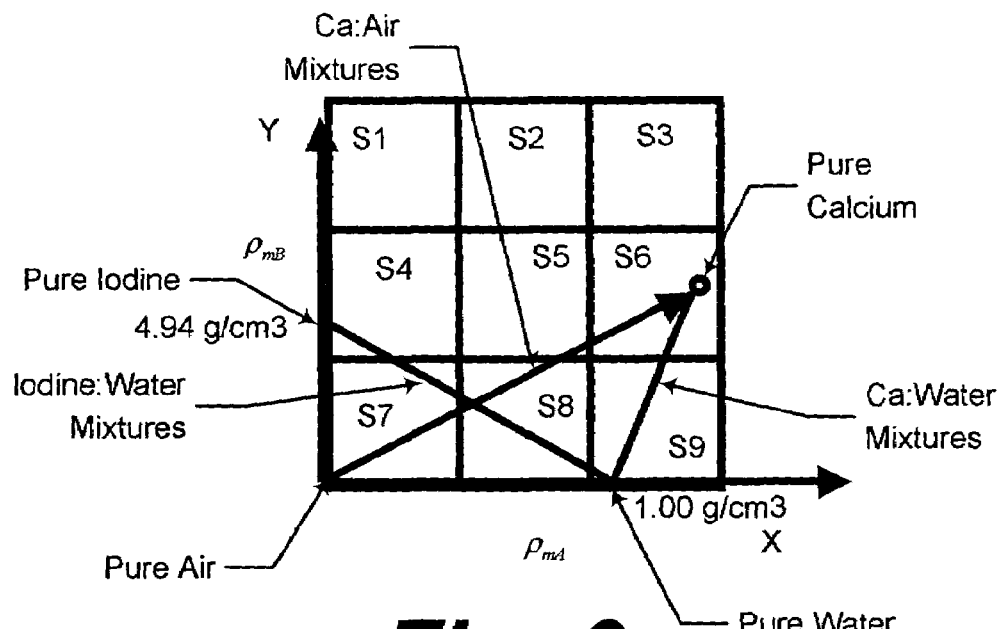
FIG. 6 is a graph illustrative of a first type of rectangular segmentation of material density regions useful in configurations of the present invention.

Ignoring k-edge effects, x-ray attenuation for any material is decomposed into a linear combination of the attenuation for two basis materials A and B. These coefficients are different for materials that have different effective atomic number. Using these different coefficients, configurations of the present invention utilize multiple material decomposition to reconstruct the material density image for any target materials. Thus, $$\alpha = \rho_{mA}\mu_A + \rho_{mB}\mu_B,$$

where $\rho_{mA}$ is a material density of basis material A having units g/cm$^3$, $\rho_{mB}$ is a material density of basis material B having units g/cm$^3$, $\mu_A$ is a mass attenuation coefficient of material A, and $\mu_B$ is a mass attenuation coefficient of material B. Referring to FIG. 6, $\rho_{mA}$ and $\rho_{mB}$ can be represented in a radial coordinate system by a radial distance written $r_m = \sqrt{\rho_{mA}^2 + \rho_{mB}^2}$ and angle written $\theta = \tan^{-1}(\rho_{mB}/\rho_{mA})$. As noted above, combinations of $\rho_{mA}$ and $\rho_{mB}$ derived from a material decomposition are distinctive for various materials including materials other than A and B, as are $r_m$ and $\theta$.

Therefore, using a predetermined mapping of material density regions, a composition of an object at each pixel (or filter pixels corresponding to one or more compositions of interest) is determined by image reconstructor and/or computer 36 at 306. The determined composition information is then used, in some configurations, to prepare an image indicative of the composition of the object (or of the locations of compositions of interest in the object) at 308.

Figure 7:
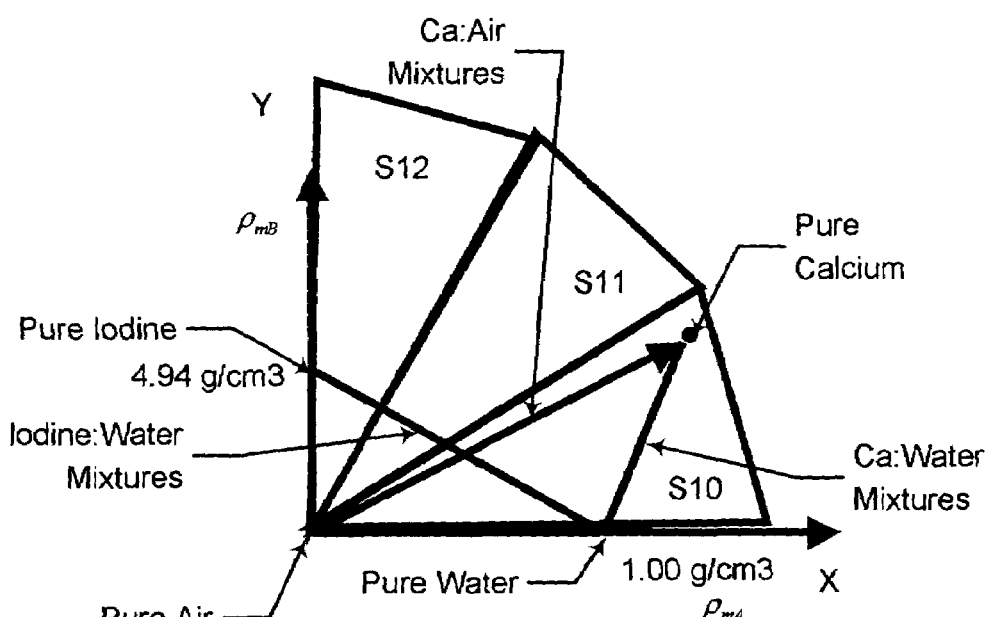
FIG. 7 is a graph illustrative of a radial segmentation of material density regions useful in configurations of the present invention.
Figure 8:
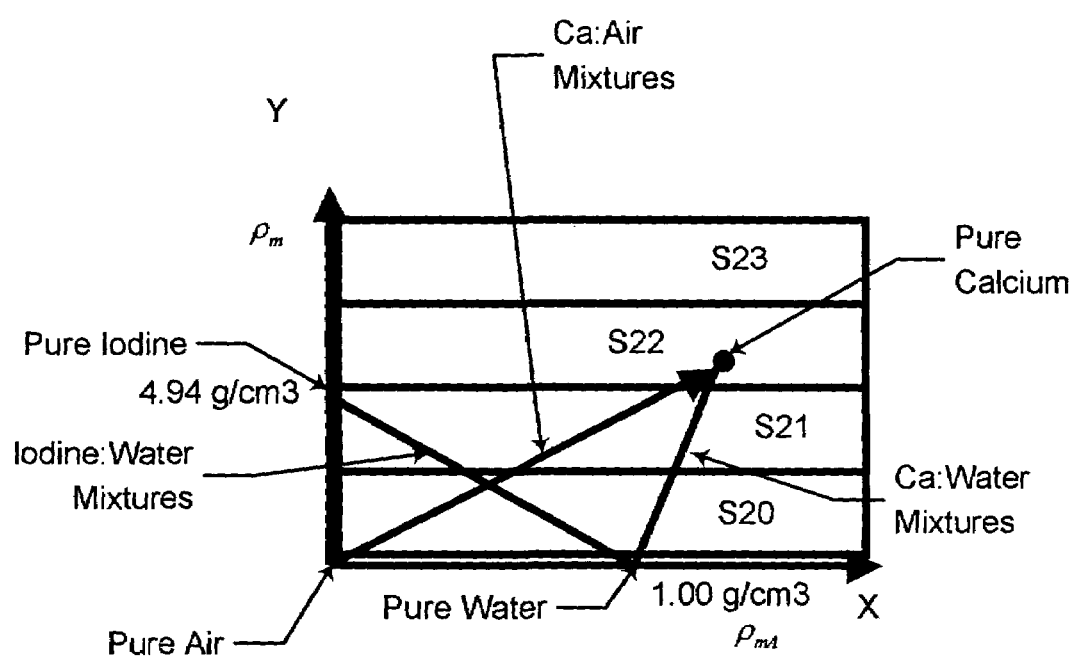
FIG. 8 is a graph illustrative of a second type of rectangular segmentation of material density regions useful in configurations of the present invention.

More particularly and referring to FIGS. 6, 7 and 8, multiple material decomposition is achieved by first acquiring dual energy measurement projection data. Any known two material decomposition method is then applied to the dual energy measurement projection data. The parameters $\rho_{mA}$ and $\rho_{mB}$ serve as x and y coordinate values in a Cartesian coordinate system, or equivalently, $r_m$ and $\theta$ serve as coordinate values in a radial coordinate system. In FIGS. 6, 7, and 8, for example, water is basis material A and iodine is basis material B, so that $\rho_w$ is an x-axis coordinate and $\rho_1$ is a y-axis coordinate. In this coordinate system, a decomposition of a pure Ca (calcium) object has coordinates x=1.188, y=0.1088. Mixtures of calcium in water fall on a line from the pure calcium coordinates to x=1, y=0, depending upon the concentration of Ca. Mixtures of air and calcium fall on a line from the pure calcium coordinates to x=0, y=0, depending upon the relative amounts of calcium and air at a given pixel point. A water-iodine mixture has coordinates on a line from x=0, y=4.94 to x=1, y=0, depending upon concentration.

To take advantage of the loci of various materials in the x-y coordinate system, regions of the plane defined by the x-y coordinates are segmented in some configurations of the present invention and assigned to a material that is most likely represented by that segment. For example, in FIG. 6, calcium, water, air, and iodine are materials of interest in a medical image, and rectangular segments S1, S2, S3, S4, S5, S6, S7, S8, and S9 are identified. Segments S1, S2, and S3 are considered "out of range" and are not associated with materials likely to be in the object being imaged. Segment S4, is indicative of large iodine concentration, although an image pixel is unlikely to fall into this segment. Segment S5 is indicative of a calcium-air mixture. Segment S6 is indicative of a high concentration of calcium. Segment S7 does not definitively indicate a composition (a pixel falling into this segment could, for example, be indicative of mostly air with some calcium, or a relatively high concentration of iodine in water). Segment S8 also does not definitively indicate a composition. Segment S9, however, is indicative of water, with either a low concentration of iodine or no more than a moderate concentration of calcium, so a pixel falling into Segment S9 is interpreted as being indicative of water.

Some configurations of the present invention use radial segmentation, as shown in FIG. 7. In FIG. 7, pie-shaped segment S10 can be interpreted as being indicative of calcium, whereas pie shaped segments S11 and S12 can be interpreted as containing no calcium.

Other configurations of the present invention use segmentation of only one of the Cartesian coordinates, as illustrated in FIG. 8. In this configuration, rectangular segments S20 and S21 are interpreted as differing iodine and/or calcium densities (concentrations) in water, assuming that no air is present in object 22 at the pixel of interest. (Assumptions such as this can be introduced in some applications of the invention by having an a priori knowledge of the composition of object 22.) Segment S22 can be interpreted as essentially pure calcium. Segment S23 is interpreted as out of range, i.e., containing no calcium, no iodine, and no water.

In some configurations of the present invention, to determine a density of a material m, it is assumed a priori that a voxel is composed of a known material. More particularly, it is assumed that $c_m$ and $d_m$ are known. Then, a dual energy measurement is performed to obtain $\rho_{mA}$ and $\rho_{mB}$ in the relationship $\alpha = \rho_{mA}\mu_A + \rho_{mB}\mu_B$. Using the material assumption ($c_m$, $d_m$), a new relationship is obtained by the relationships $c_m\rho = \rho_{mA}$ and $d_m\rho = \rho_{mB}$, where $\rho$ is the density of material m. A ratio $R = \rho_{mA}/\rho_{mB} = c_m/d_m$ is then determined, which is independent of $\rho$.

For a particular pair of basis materials A and B, such as water and iodine, the combination of $c_m$ and $d_m$ can be assumed to be unique for any other material, and the ratio R can also be assumed to be unique. The ratio R is then used to identify the material m in a particular voxel or pixel element. For example, the ratio R falls into one of a plurality of predetermined ranges, each corresponding to a limited number of target materials. Ranges of this ratio correspond to angular segments of a rectangular plot, such as segments S10, S11, and S12 shown in FIG. 6. However, in some configurations, there can usefully be as few as two segments or as many segments as can be accommodated within the available precision and noise limitations of the CT imaging system. The ranges of R are determined in accordance with ratios that would be obtained for various materials of interest (e.g., calcium, water, iodine, etc.), and the rectangular plot is divided into a limited number of sectors. The segments are not necessarily of equal size, but each segment represents a limited, predetermined range of material compositions.

Thus, some configurations of the present invention selectively display only image pixels within a certain range $R_{min} \leq R \leq R_{max}$ to display an image showing the locations of a selected material within an object 22. $R_{min}$ and $R_{max}$ are determined in advance for any particular material to be displayed. Other materials have R values outside this range and are not shown in the image.

For example, a phantom containing gadolinium (Gd), calcium (Ca) and iodine (I) at specific locations was scanned by a conventional CT imaging system. The reconstructed image clearly showed the location of each element, but the composition of the spots indicative of these locations could not be determined from the image. By performing a multiple material decomposition, images showing only iodine locations free of contamination of other materials were produced by indicating only locations at which $0 \leq R \leq 1$. Calcium was shown in a separate image produced by indicating only locations at which $10 \leq R \leq 12$. Gadolinium was shown in a separate image produced by indicating only locations at which $35 \leq R \leq 37$.

It is not necessary that the basis materials or the segmentation of coordinates or of the ratio R be predetermined by a manufacturer, or that imaging apparatus 10 of the present invention be committed to specific basic materials and/or restricting the set of materials that can be identified. Instead, in some configurations of the present invention and as noted above, a user is able to select his or her own set of basis materials and generate a composition matrix as described in connection with FIG. 4. Also, although preprogrammed segmentations and/or ratio ranges can be provided to a user for one or more sets of basis materials, some configurations of the present invention permit a user to specify his or her own segmentation. The user can determine such segmentations empirically or otherwise, to suit his or her own needs. In cases in which the user chooses the basis materials, the basis materials are referred to herein as being "preselected" if the selection is done prior to the scanning of an object. On the other hand, the term "postselected" refers to a selection of basis materials made after the scanning of an object. The term "selected" is used herein to broadly encompass either case. The determination of segmentation may also occur before or after a scan is performed. When broadly referring to either case, the term "determined" is used, rather than the less inclusive "predetermined" or "postdetermined."

Figure 9:
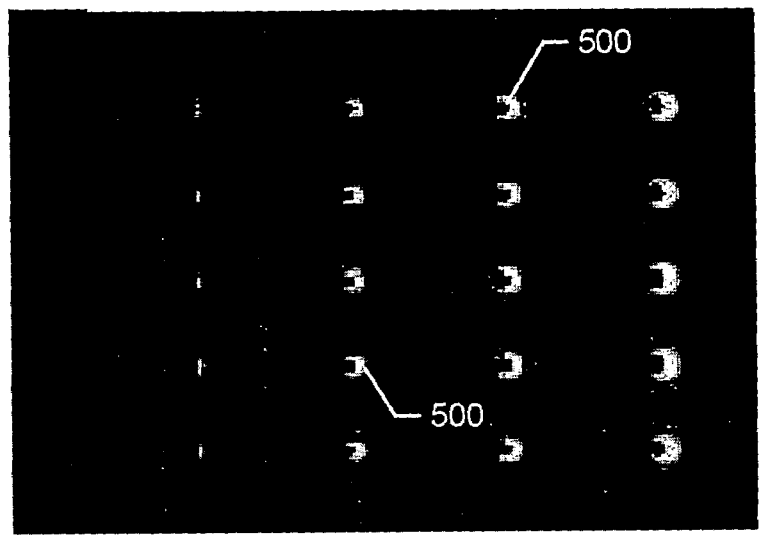
FIG. 9 is a multiple material decomposition iodine image of blocked lumens in a phantom produced by a configuration of the present invention.
Figure 10:
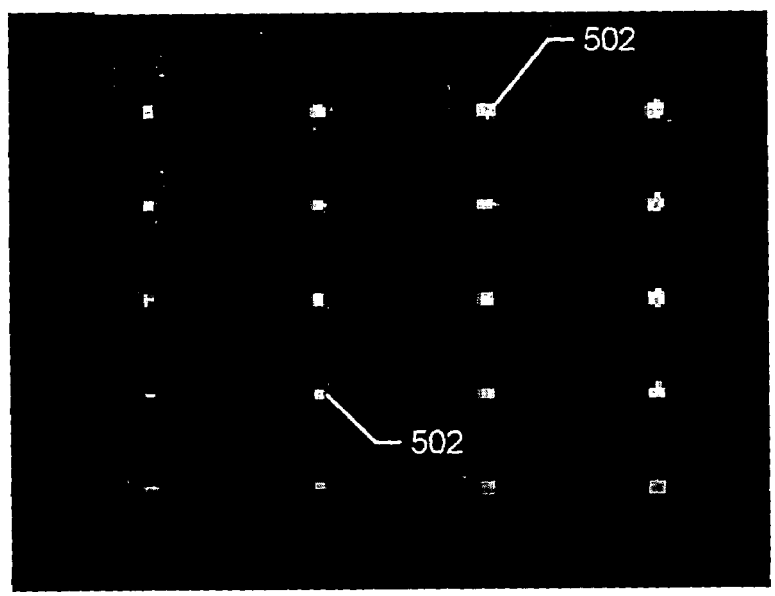
FIG. 10 is a multiple material decomposition calcium image of blocked lumens in the phantom of FIG. 9, also produced by a configuration of the present invention.
Figure 11:
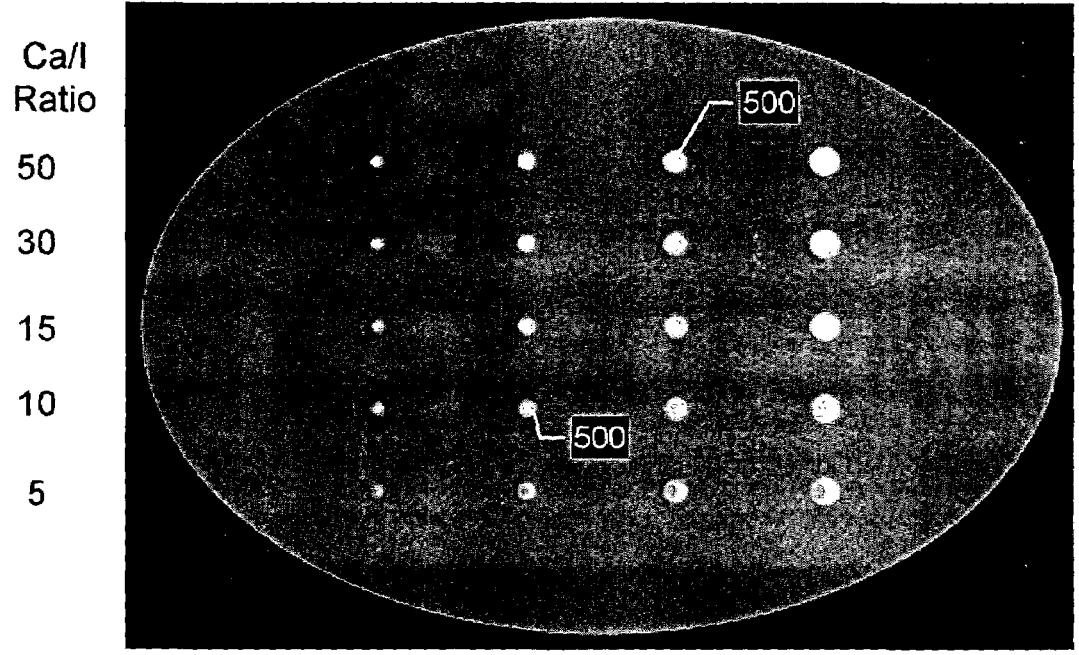
FIG. 11 is a conventional, prior art CT image of the blocked lumens in the phantom of FIG. 9, presented for comparison with FIGS. 9 and 10.

The usefulness of various configurations of the present invention is revealed in FIGS. 9 and 10, which show true lumen 500 shape and calcium blockage 502 in a simulation phantom obtained by multiple material decomposition over a complete range of Ca/I ratios. By contrast, and referring to FIG. 11, conventional CT imaging is essentially unable to show simulated calcium blockages in lumens 500 of the simulation phantom.

In still other configurations of the present invention, a gray scale image is usefully displayed in accordance with values of $\rho = (\rho_{mA}/c_m + \rho_{mB}/d_m)/2$.

It will be recognized that configurations of the present invention are capable of providing quantitative material information. In configurations of the present invention, only one material (subject to an overall system material separate sensitivity) is reconstructed with the correct density for each image, thereby improving target material visibility and quantification accuracy. Configurations of the present invention also can provide decomposition into more than one material.

The present invention is useful for various applications that use a ratio between the two basis material images to perform multiple material decomposition, tissue segmentation, or material quantification.

While the invention has been described in terms of various specific embodiments, those skilled in the art will recognize that the invention can be practiced with modification within the spirit and scope of the claims.

What is claimed is:

1. A method for analyzing materials in an object, said method comprising:
   acquiring x-ray projection data of the object at high energy and at low energy for a plurality of views;
   utilizing the acquired x-ray projection data in a material decomposition to determine material densities at each pixel for two selected basis materials;
   determining a composition of an object at each pixel utilizing a determined mapping of material density regions for the two selected basis materials; and
   displaying an image indicative of the composition of the object utilizing the determined composition;
   wherein said selected materials are predetermined, said determining a composition of an object at each pixel utilizing a predetermined mapping of material density regions for the two preselected materials comprises determining which of a plurality of rectangular regions in a Cartesian coordinate system contains said determined material densities, and selecting the determined composition in accordance with said determined rectangular region or determining a ratio of said determined material densities, and selecting the determined composition in accordance with said ratio.

2. A method in accordance with claim 1 wherein said acquiring of x-ray projection data comprises performing a computed tomographic scan of the object.

3. A method in accordance with claim 1 wherein said utilizing the acquired x-ray projection data in a material decomposition to determine material densities at each pixel for two selected materials comprises performing a table lookup.

4. A method in accordance with claim 1 wherein said selected materials are water and iodine.

5. A method in accordance with claim 1 wherein said selected materials are preselected, and said determined mapping of material density regions is a predetermined mapping.

6. A method for analyzing materials in an object, said method comprising:
acquiring x-ray projection data of the object at high energy and at low energy for a plurality of views;
utilizing the acquired x-ray projection data in a material decomposition to determine material densities at each pixel for two selected basis materials;
utilizing a determined mapping of material density regions for the two selected basis materials, filtering pixels of an image of the object corresponding to one or more compositions of interest; and displaying an image indicative of the locations of composition of interest of the object;
wherein said selected materials are predetermined, and wherein the method further comprises determining a composition of an object at each pixel utilizing a predetermined mapping of material density regions for the two preselected materials by determining which of a plurality of rectangular regions in a Cartesian coordinate system contains said determined material densities, and selecting the determined composition in accordance with said determined rectangular region or determining a ratio of said determined material densities, and selecting the determined composition in accordance with said ratio.

7. A method in accordance with claim 6 wherein said acquiring of x-ray projection data comprises performing a computed tomographic scan of the object.

8. A method in accordance with claim 6 wherein said utilizing the acquired x-ray projection data in a material decomposition to determine material densities at each pixel for two selected materials comprises performing a table lookup.

9. A method in accordance with claim 6 wherein said selected materials are water and iodine.

10. A method in accordance with claim 6 wherein said selected materials are preselected, and said determined mapping of material density regions is a predetermined mapping.

11. A method in accordance with claim 6 wherein the object comprises a blocked lumen, and said image indicative of the locations of composition of interest of the object comprises an image indicative of locations of blockage in the blocked lumen.

12. An apparatus for analyzing materials in an object, said apparatus comprising an x-ray source and a detector configured to acquire projection data at high and low energies for a plurality of views, a computer, a storage device, and a display, comprising:
means for acquiring x-ray projection data of the object at high energy and at low energy for a plurality of views utilizing said x-ray source and said detector;
means for processing the acquired x-ray projection data utilizing said computer and said storage device to determine material densities at each pixel for two selected basis materials;
means for determining a composition of an object at each pixel utilizing said computer and a determined mapping of material density regions for the two selected basis materials in said storage device; and
means for utilizing said display to display an image indicative of the composition of the object utilizing the determined composition;
wherein selected materials are predetermined, said means for determining is configured to determine which of a plurality of rectangular regions in a Cartesian coordinate system contains said determined material densities, and to select the determined composition in accordance with said determined rectangular region or determine a ratio of said determined material densities, and to select the determined composition in accordance with said ratio.

13. An apparatus in accordance with claim 12 wherein said x-ray source and said detector are on a rotating gantry, and wherein said means for acquiring is configured to perform a computed tomographic scan of the object.

14. An apparatus in accordance with claim 12 wherein said means for determining determines material densities at each pixel, via a table lookup.

15. An apparatus in accordance with claim 12 wherein said selected materials are preselected, and said determined mapping of material density regions is a predetermined mapping.

16. An apparatus for analyzing materials in an object, said apparatus comprising an x-ray source and a detector configured to acquire projection data at high and low energies for a plurality of views, a computer, a storage device, and a display, comprising:
means for acquiring x-ray projection data of the object at high energy and at low energy for a plurality of views utilizing said x-ray source and said detector;
means for processing the acquired x-ray projection data utilizing said computer and said storage device to determine material densities at each pixel for two selected basis materials;
means for utilizing said computer and a determined mapping of material density regions for the two selected basis materials in said storage device to filter pixels of an image of the object corresponding to one or more compositions of interest; and
means for utilizing said display to display an image indicative of the locations of composition of interest of the object;
wherein said selected materials are predetermined, said means for utilizing said computer and determined mapping of density regions for the two selected basis materials is configured to determine which of a plurality of rectangular regions in a Cartesian coordinate system contains said determined material densities, and to select the determined composition in accordance with said determined rectangular region or determine a ratio of said determined material densities, and to select the determined composition in accordance with said ratio.

17. An apparatus in accordance with claim 16 wherein said x-ray source and said detector are on a rotating gantry, and wherein said means for acquiring is configured to perform a computed tomographic scan of the object.

18. An apparatus in accordance with claim 16 wherein said means for utilizing determines material densities at each pixel for two selected materials, via a table lookup.

19. An apparatus in accordance with claim 16 wherein said selected materials are preselected, and said determined mapping of material density regions is a predetermined mapping.

* * * * *